(12) United States Patent
Rajaiah et al.

(10) Patent No.: US 8,835,529 B2
(45) Date of Patent: Sep. 16, 2014

(54) DENTURE ADHESIVE COMPOSITIONS

(71) Applicant: The Procter & Gamble Company, Cincinnati, OH (US)

(72) Inventors: Jayanth Rajaiah, Loveland, OH (US); Arif Ali Baig, Mason, OH (US); Robert Scott Leonard, Fairfield, OH (US)

(73) Assignee: The Procter & Gamble Co., Cincinnnati, OH (US)

(*) Notice: Subject to any disclaimer, the term of this patent is extended or adjusted under 35 U.S.C. 154(b) by 0 days.

(21) Appl. No.: 13/644,934

(22) Filed: Oct. 4, 2012

(65) Prior Publication Data

US 2014/0100303 A1   Apr. 10, 2014

Related U.S. Application Data

(60) Provisional application No. 61/546,119, filed on Oct. 12, 2011.

(51) Int. Cl.
   *A61C 13/23* (2006.01)
   *A61K 6/00* (2006.01)

(52) U.S. Cl.
   CPC .................................. *A61K 6/0026* (2013.01)
   USPC ........................................................ 523/120

(58) Field of Classification Search
   USPC ........................................................ 523/120
   See application file for complete search history.

(56) References Cited

U.S. PATENT DOCUMENTS

| | | | |
|---|---|---|---|
| 2,047,398 | A | 7/1936 | Voss et al. |
| 2,782,182 | A | 2/1957 | Verburg |
| 3,003,988 | A | 10/1961 | Germann et al. |
| 3,736,274 | A | 5/1973 | Schoenholz et al. |
| 4,373,036 | A | 2/1983 | Chang et al. |
| 4,470,814 | A | 9/1984 | Chang et al. |
| 4,521,551 | A | 6/1985 | Chang et al. |
| 4,569,955 | A | 2/1986 | Dhabhar |
| 4,758,630 | A | 7/1988 | Shah et al. |
| 4,980,391 | A | 12/1990 | Kumar et al. |
| 4,989,391 | A | 2/1991 | Wetter |
| 5,006,571 | A | 4/1991 | Kumar et al. |
| 5,037,924 | A | 8/1991 | Tazi et al. |
| 5,073,604 | A | 12/1991 | Holeva et al. |
| 5,093,387 | A | 3/1992 | Schobel et al. |
| 5,204,414 | A | 4/1993 | Pelah et al. |
| 5,304,616 | A | 4/1994 | Rajaiah et al. |
| 5,525,652 | A | 6/1996 | Clarke et al. |
| 5,658,586 | A | 8/1997 | Rajaiah et al. |
| 5,753,723 | A | 5/1998 | Chang et al. |
| 5,830,933 | A | 11/1998 | Synodis et al. |
| 6,025,411 | A | 2/2000 | Wong et al. |
| 6,110,989 | A | 8/2000 | Clarke |
| 6,239,191 | B1 | 5/2001 | Wong et al. |
| 6,677,391 | B1 | 1/2004 | Rajaiah et al. |
| 2011/0223563 | A1 | 9/2011 | Rajaiah et al. |

OTHER PUBLICATIONS

International Search Report with Written Opinion. date mailed Feb. 18, 2013; 9 pages.

*Primary Examiner* — Nicole M Buie-Hatcher
*Assistant Examiner* — Chelsea M Lowe
(74) *Attorney, Agent, or Firm* — James E. Oehlenschlaeger (57) ABSTRACT

A denture adhesive composition having a denture adhesive component and a cohesion builder component. The cohesion builder component may be of salts of mono-phosphates, salts of di-phosphates, or salts of tri-phosphates.

12 Claims, 2 Drawing Sheets

DENTURE ADHESIVE COMPOSITIONS

FIELD OF THE INVENTION

The present disclosure relates to denture adhesive compositions. More particularly, the present disclosure relates to compositions including a denture adhesive component and a cohesion builder component.

BACKGROUND OF THE INVENTION

Ordinary removable dentures, dental plates and the like, comprise teeth mounted in a suitable plate or base. Denture stabilizers, including denture adhesives, are used to fill the interstices between the dentures and the gums or tissues. Prior to placement of the denture in the oral cavity, a denture stabilizer is applied to the denture-plate surface which, for a perfect fit, should uniformly contact the gums and mucous tissues. The denture stabilizer is formulated not only for its adherent properties, but also to provide a cushion or gasket between the denture and the gums or tissues, thereby positioning the denture securely in the oral cavity.

Considerable effort has been made over the years to develop improved denture adhesive compositions. Both synthetic and natural polymers and gums have been used singly, in combination, and in combination with various adhesives and other materials in an attempt to lessen certain deficiencies. These deficiencies include inadequate holding power and messiness and difficulty of removing the residual adhesive from the mouth and dentures. Also, food may become trapped between the denture and the oral cavity of the wearer. Additionally, certain components may present a less than desirable taste to the wearer.

Despite the above-noted technologies, as well as many others, a need still exists for denture stabilizing compositions providing good hold.

SUMMARY OF THE INVENTION

A denture adhesive composition is provided that comprises a denture adhesive component in an amount from about 20.0% to about 70.0% by weight of the denture adhesive composition; wherein the denture adhesive component comprises a mixture of a partial salt of a copolymer of methyl vinyl ether-maleic acid and sodium carboxy methyl cellulose; and a cohesion builder component in an amount from about 0.001% to about 10% by weight of the denture adhesive composition; wherein the cohesion builder component is at least one of salts of mono-phosphates, salts of di-phosphates, or salts of tri-phosphates.

A denture adhesive composition is provided that comprises a denture adhesive component in an amount from about 20.0% to about 70.0% by weight of the denture adhesive composition; wherein the denture adhesive component comprises a mixture of a partial salt of a copolymer of methyl vinyl ether-maleic acid and sodium carboxy methyl cellulose; wherein the partial salt of copolymer of methyl vinyl ether-maleic acid contains a cationic salt function having from about 60% to about 72% calcium cations; from about 0% to about 10% sodium cations; and from about 20% to about 40% of a free acid component; a cohesion builder component from about 0.1% to about 2.0% of the denture adhesive composition, wherein the cohesion builder component comprises dibasic sodium phosphate; and a water insoluble component from about 20% to about 70% by weight of the denture adhesive composition.

BRIEF DESCRIPTION OF THE DRAWINGS

While the specification concludes with claims which particularly point out and distinctly claim the subject matter that is regarded as the invention, it is believed the various embodiments will be better understood from the following description taken in conjunction with the accompanying drawings, in which:

DETAILED DESCRIPTION OF THE INVENTION

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

DEFINITIONS

The term "denture" as used herein refers to the upper or lower denture, a partial upper or lower denture, or any combination of partial and full dentures.

The term "denture adhesive article" and/or "article" as used herein refers to articles designed to fit, conform and adhere to contoured surfaces, such as a denture, as well as the gums or the roof of the mouth. The articles herein are substantially solid prior to use and can be picked up manually in substantially one piece and positioned on the denture. They are also preformed, that is, they are pre-shaped and ready to be applied.

The term "cohesion" as used herein refers to the internal resistance to flow or deformation of a material. This can be measured by the extent of flow of a material under stress. In one embodiment, this can be measured by the extent of flow under gravitational stress. In other embodiments, rheological parameters such as loss modulus G", storage modulus G', or rheological-Creep, may be measured.

The term "cohesion builder" as used herein refers to a material which increases the cohesion of the denture adhesive component when hydrated. This hydration may be done suitably with distilled water.

The term "phosphate" as used herein refers to a salt or ester of phosphoric acid. The term "mono-phosphate" as used herein refers to phosphates that contain one atom of phosphorous. The term "di-phosphate" as used herein refers to phosphates that contain two atoms of phosphorous. The term "tri-phosphate" as used herein refers to phosphates that contain three atoms of phosphorous.

By "safe and effective amount", as used herein, is meant an amount of an agent high enough to significantly (positively)

modify the condition to be treated or positively modify the benefit sought, but low enough to avoid serious side effects (at a reasonable benefit/risk ratio), within the scope of sound medical/dental judgment. The safe and effective amount of an agent may vary with the particular condition being treated, the age and physical condition of the patient being treated, the severity of the condition, the duration of treatment, the nature of concurrent therapy, the specific form of the source employed, and the particular vehicle from which the agent is applied.

The term "AVE/MA" as used herein refers to alkyl vinyl ether-maleic acid or anhydride copolymer. The term "mixed salts", as used herein, refers to salts of polymers, such as AVE/MA, where at least 2 different cations are mixed on the same polymer with each other or with other salts. The term "partial salts", as used herein, refers to salts of polymers, such as AVE/MA, wherein less than 100% of the acid groups are reacted. The term "free acid" (FA), as used herein, refers to the un-reacted acid groups of polymers such as AVE/MA. The percentages used herein to describe the cationic salt function of the alkyl vinyl ether-maleic acid or anhydride copolymers are defined as the stoichiometric percent of the total initial carboxyl groups reacted on the polymer.

The term "non-aqueous", as used herein, means no free water is added to the composition, but the composition may contain about 5% or less of water by weight of the composition, which comes in as part of other components.

The term "water-insoluble" as used herein refers to a material that, when exposed to water, does not dissolve, but may disperse to varying degrees. Generally, a material is water-insoluble if it is less than about 10% soluble in water.

The term "thermoplastic" as used herein refers to a material that melts, softens, becomes more flexible, extrudable, deformable, shapable, moldable, flowable, processable, and/or changes rheology when exposed to heat. In one embodiment the material generally solidifies, hardens, and/or substantially returns to its original condition, when subsequently cooled.

The term "bioerodible" as used herein means that the composition, when exposed to water or saliva, will erode over time due to physical and/or chemical action. The composition may erode completely or substantially, however ultimately the composition will lose its original form and/or integrity. For example, after application and use for at least about 24 hours in the oral cavity the composition will not have sufficient product integrity to easily separate or peel, in its original form, from the denture or oral surface.

Unless otherwise noted, the term "derivative" as used herein refers to when the primary polymeric backbone is left unchanged, but the side groups/chains and/or end groups are changed.

As used herein, the term "silicone" refers to siloxane polymers based on a structure of alternate silicon and oxygen atoms with various organic radicals attached to the silicon.

The phrase "substantially free of" as used herein means in certain embodiments 0% or less than 0.0001%, less than 0.001%, less than 0.01%, or less than 0.1%, by weight of the composition.

All other percentages used herein are by weight of the composition unless otherwise indicated.

Denture Adhesive Compositions and Methods

In general, denture adhesive compositions according to the present disclosure include a denture adhesive component and a cohesion builder component.

Denture adhesive compositions have become a daily product for many people who are looking for better fit and/or more security when wearing dentures. This has driven consumer demand for products which have improved properties like long lasting hold, strong hold and/or resistance to dilution/washout, for example. The present denture adhesive compositions deliver improvements on such desirable properties.

In general, denture adhesive compositions comprise a denture adhesive component (salts of AVE/MA, and/or sodium carboxy methyl cellulose, for example) dispersed in a water insoluble component (petrolatum, and/or mineral oil, for example). During use, the moisture in the saliva penetrates through the water insoluble component and hydrates the denture adhesive component. This makes the denture adhesive component cohesive and sticky to the mucosal tissue and denture surface.

As stated in U.S. Pat. No. 6,025,411, "There are a number of desirable characteristics of a denture fixative composition. One extremely desirable attribute is that it develops a high degree of tack upon contact with saliva so that the dentures can be held in place as soon as they are seated in the mouth. It is also highly desirable that the mucilage be spread over the denture-mucosa interface in order to effectively seal the denture in place and that the mucilages possess sufficient cohesive strength to withstand the stresses of mastication which act to rupture the seal and thus dislodge the denture. The denture fixative must also exhibit sufficient resistance to degradation under the extreme environmental changes that occur in the oral cavity during such common actions as drinking coffee or other hot beverages." Another desirable attribute is that denture adhesives must also develop cohesive strength quickly when hydrated with moisture or saliva. The cohesion of the hydrated mass should be great enough to securely maintain the position of the denture, and offer resistance to salivary washout.

Over the years there have been many approaches tried to increase the cohesion/strength of denture adhesives. Examples of this include crosslinked poly acrylic acids, as described in U.S. Pat. No. 4,470,814, crosslinked AVE/MA, as described in U.S. Pat. No. 4,521,551, reacting AVE/MA with divalent metals, as described in U.S. Pat. No. 5,525,652, and, adding a non-adhesive self-supporting layer that is characterized by its ability to maintain strength and provide integrity for the adhesive composition in the presence of water and/or saliva, as described in U.S. Pat. No. 5,658,586. An adhesion promoter may also be added to a fixative composition to improve the tackiness while maintaining the cohesive strength constant, as described in U.S. Pat. No. 5,753,723. Further, as stated in U.S. Pat. No. 5,830,933, "In order to provide additional adhesive and cohesive properties, one approach which has been taken is to manipulate the salt form of the copolymer. Examples can be found in WO 92/22280, WO 92/10988, WO 92/10987 and U.S. Pat. Nos. 4,758,630 and 5,073,604. Another approach has been to employ an adhesion adjuvant in the formulation or converting the copolymer into a terpolymer, and examples of these approaches can be found in U.S. Pat. Nos. 3,736,274, 5,037,924 and 5,093,387."

The technical literature discloses a wide variety of denture adhesive materials. However, most presently available commercial denture adhesives are based on alkyl vinyl ether/maleic acid or anhydride copolymers. This class of adhesives was set forth as a potential denture adhesive in Germann et al., U.S. Pat. No. 3,003,988. The Germann et al '988 patent describes synthetic, water sensitized but water insoluble, materials comprising mixed partial salts of lower alkyl vinyl ether-maleic anhydride copolymers for stabilizing dentures.

The salts mentioned are a mixture of (a) calcium and (b) alkalies including sodium, potassium and quaternary ammonium compounds.

The calcium and alkali materials are added to the copolymer to form a mixed salt. The use of this class of materials has been described in a variety of other patents. Examples include U.S. Pat. Nos. 4,989,391, 5,037,924, 5,093,387, 4,980,391 and 4,373,036, European Published Patent Application No. 406,643 and WO 92/10988.

The denture adhesive composition can take many different forms from a liquid to a solid. For example, the composition can be an emulsion, dispersion, slurry, gel, cream, paste, strip, wafer, and mixtures thereof. In one embodiment, the denture adhesive composition is in the form of a gel, cream, or paste. In another embodiment, the denture adhesive composition is in the form of a liner. In an additional embodiment, the denture adhesive composition is not a preformed article. In another embodiment, the denture adhesive composition can be extruded out of a nozzle of a container like a tube, syringe, and/or pump, for example, directly onto a denture surface or a surface of the oral cavity. In further embodiments, the ratio of the cross-sectional area of the barrel to the cross-sectional area of the nozzle on the container is from about 50, 30, 20, 15, 10, 8, and/or 5 to about 15, 10, 8, 5, 2, and/or 1 and/or any combination thereof.

In one embodiment, the denture adhesive composition is in the form of an article.

Regardless of the form of dispensing the article, including but not limited to pre-dosed ready to use articles and/or articles which are dispensed from, for example, a tube, articles are substantially solid prior to use and can be picked up manually. Denture adhesive articles that can be dispensed from a tube can be identified as articles by the following method:

1. Fill the product into a tube with a 0.16" diameter nozzle.
2. Extrude a 1" long strip of the product onto a denture tile (1.5"×1.5" square tile made from denture-plastic) taking care to hold the nozzle about ⅛" above the denture tile. Do not touch the nozzle to the denture tile while extruding the product.
3. After about 1" of product has been extruded, hold the nozzle about ⅛" above the denture tile and use a spatula to cut the strip against the nozzle. Do not touch or smear the nozzle against the denture tile while cutting the strip.
4. Use the thumb and forefinger to hold the middle of the strip and pick it up vertically off the denture tile. Do not use a wiping motion of the fingers against the denture tile.
5. The composition is an article if it can be picked up in substantially one piece.

Substantially in one piece means, as used herein, that from about 75%, 80%, 85%, 90% to about 100%, 90%, 85%, 80%, 75%, 70% and/or any combination thereof of the denture adhesive composition remains in one piece when manually picked up from the oral surface.

Some denture adhesive articles are pre-dosed and/or ready to use. A user may be able to identify these items visually as a denture adhesive article, as they are often in the form of a strip contained within a package. However, if not evident that these denture adhesive products are articles, these denture adhesive articles can be identified as articles by the following method:
1. Shape the composition into a sheet about 0.67 mm thick× about 8 mm wide×about 44 mm long.
2. Place sheet on a denture tile.
3. Use fingers to pick up sheet.
4. The composition is an article if it can be picked up in substantially one piece.

In addition to taking many forms, the denture adhesive composition can also take many shapes. These shapes include, for example, symmetrical and asymmetrical concave shapes, lines, dots, dashes, flat, rounded, etc.

The denture adhesive composition also has many properties. In one embodiment, the composition has a property selected from the group consisting of: bioerodible, non-aqueous, and mixtures thereof.

In certain embodiments, the denture adhesive composition comprises 0% or less than 0.0001%, less than 0.001%, less than 0.01%, or less than 0.1% by weight of the composition of: water, polyethylene oxide, Eudragit, cellulose, acrylic, polydimethylsiloxene, room temperature vulcanizing compositions, two-part compositions, epoxies, water soluble thermoplastic components, non-crystalline thermoplastic components, zinc, hydrophobic acetate, acrylic ester, polyvinyl alcohol, poly phosphate, polyethylmethylacrylate (PEMA), polymethylmethylacrylate (PMMA), polybutylmethylacrylate (PBMA), and/or combinations thereof.

In certain embodiments the composition of the present disclosure must be cleaned off of the denture after use, cannot be easily removed from the denture once applied, and/or easily separated from the denture after it has been used in the mouth. In certain embodiments the composition of the present disclosure erodes within three days and is not capable of being used for a period of for example one week to a few weeks. In certain embodiments the composition of the present disclosure is not a self-supporting and shape-retaining layer in the form of a sheet, and/or, a liner that can be used over one to three days. In certain embodiments the composition of the present disclosure does not cure and set, is not self-supporting, does not retain its shape, is not in the form of a sheet, is not rubber-like, is not flexible, and/or is not a liner.

Denture Adhesive Component

In one embodiment, the denture adhesive compositions include a safe and effective amount of a denture adhesive component, generally at a level from about 5% to about 90% by weight of the denture adhesive composition. In other embodiments, the denture adhesive component is in the range from about 5%, 10%, 15%, 20%, 25%, 30%, 35%, 40%, 45%, 50% to about 20%, 30%, 40%, 50%, 55%, 60%, 70%, 80%, 90% or any combination thereof. In other embodiments, the composition includes at least about 20% or at least about 30% by weight of the composition of a denture adhesive component.

In general, denture adhesive components are hydrophilic particles that become sticky when activated by moisture. For those that activate with moisture, moisture can be present, for example, in the denture adhesive composition itself as well as in the oral cavity of the user. In varying embodiments, the denture adhesive components herein are mucoadhesive, hydrophilic, water soluble, have the property of swelling upon exposure to moisture, form a mucilaginous mass when combined with moisture, or any combination thereof. In a further embodiment the denture adhesive component may be selected from the group consisting of: poloxamer, Sorbitol, polyox, carbomer, polyacrylamides, poly peptides, natural gums; synthetic polymeric gums; AVE/MA; AVE/MA/IB; copolymers of maleic acid or anhydride and ethylene, styrene, and/or isobutylene, polyacrylic acid and/or polyacrylates thereof; polyitaconic acid, mucoadhesive polymers; water-soluble hydrophilic colloids; saccharide; cellulose; their derivatives, and combinations thereof. Examples of such materials include karaya gum, guar gum, gelatin, algin, sodium alginate, tragacanth, chitosan, acrylamide polymers, carboxypolymethylene, polyvinyl alcohol, polyamines, polyquarternary compounds, polyvinylpyrrolidone, polyvinylpyrrolidone copolymers, cationic polyacrylamide polymers, salts and mixed salts of AVE/MA, salts and mixed salts of AVE/MA/IB, salts and mixed salts of AVE/MA/Styrene, salts and mixed salts of AVE/MA/Ethylene; polymeric acids, polymeric salts, and copolymers thereof; polyitaconic acid salts, polyhydroxy compounds, their derivatives, and combinations thereof.

In one embodiment the denture adhesive component may be selected from the group consisting of salts of AVE/MA, mixed salts of AVE/MA, cellulose derivatives (such as methylcellulose, carboxymethylcellulose, hydroxyethylcellulose, hydroxypropylcellulose, hydroxy-propylmethylcellulose, corn starch, and combinations thereof), polyethylene glycol, karaya gum, sodium alginate, chitosan, and combinations thereof. In yet another embodiment, the adhesive component may be selected from the group consisting of mixed salts of AVE/MA, cellulose derivatives, and combinations thereof.

In another embodiment, the denture adhesive component may be selected from the group consisting of: cellulose, cellulose derivatives, starch, starch derivatives, saccharide, saccharide derivatives, polyethylene oxides, polyethylene glycols, polyvinyl alcohols, carrageenan, alginates, karaya gums, xanthan gums, guar gums, gelatins, algins, tragacanth, chitosan, acrylamide polymers, carboxypolymethylenes, polyamines, poly quaternary compounds, polyvinylpyrrolidone, AVE/MA, salts of AVE/MA, parital salts of AVE/MA, mixed salts of AVE/MA, polymeric acids, polymeric salts, polyhydroxy compounds, and combinations thereof.

In one embodiment, the adhesive component may be a salt of a polymer of AVE/MA. In another embodiment, the adhesive component may be a partial salt of a polymer of AVE/MA. In another embodiment the adhesive component includes a mixed partial salt of a polymer of AVE/MA. In a further embodiment, the AVE/MA copolymer contains a cationic salt function including a cation selected from the group consisting of: Group IA and Group IIA cations of the periodic table, yttrium, titanium, zirconium, vanadium, chromium, manganese, iron, nickel, copper, zinc, boron, aluminum, and combinations thereof. In another embodiment, the adhesive component may be a partial salt of an AVE/MA copolymer containing a cationic salt function comprising a cation selected from the group consisting of strontium, zinc, iron, boron, aluminum, vanadium, chromium, manganese, nickel, copper, yttrium, titanium, magnesium, calcium, sodium, and combinations thereof. In yet another embodiment the cation may be selected from the group consisting of strontium, zinc, iron, magnesium, calcium, sodium, and combinations thereof. In yet another embodiment, the cation may be selected from the group consisting of strontium, iron, magnesium, calcium, sodium, and combinations thereof. In one embodiment, the adhesive component includes a calcium and sodium mixed partial salt of an AVE/MA copolymer. In another embodiment, the denture adhesive component includes AVE/MA, salts of AVE/MA, partial salts of AVE/MA, mixed salts of AVE/MA, sodium carboxymethylcellulose, or combinations thereof. In another embodiment, the denture adhesive component may be a combination of a partial salt of AVE/MA and carboxymethylcellulose. In another embodiment, the denture adhesive component may be a combination of a mixed partial salt of AVE/MA and carboxymethylcellulose.

The AVE/MA copolymers may have a range of specific viscosities. For example, the specific viscosity may be at least 2.0, alternatively 2.5 or higher, alternatively from about 2.5 to about 5, when measured as a 1% weight/volume solution of the starting anhydride or acid of the copolymer, in methyl ethyl ketone at 25° C. In one embodiment, the salt of a copolymer of alkyl vinyl ether-maleic acid or anhydride has a specific viscosity of from about 2.5 to about 3.8 when measured as a 1% in methyl ethyl ketone solution at 25° C.

The AVE/MA copolymers may have a molecular weight of at least about 1,250,000 daltons. In certain embodiments, the molecular weight is from about 1,500,000 to about 3,000,000, alternatively from about 1,700,000 to about 2,100,000 or from about 1,800,000 to about 2,000,000 daltons.

AVE/MA copolymers commercially available and useful herein include GANTREZ AN169 or GANTREZ 179, available from International Specialty Products, having a typical molecular weight of about 1,980,000 and 2,400,000 respectively, per their brochure materials. Another suitable polymer commercially available is AN169 BF, also from International Specialty Products.

In certain embodiments, the AVE/MA copolymers may be reacted to form a salt containing a cationic salt function. In certain embodiments, the AVE/MA copolymers may be reacted to form a partial salt containing a cationic salt function. In certain embodiments, the cationic salt function may comprise from about 60% to about 72% of cations selected from calcium, strontium, magnesium and combinations thereof. In certain embodiments, the cationic salt function comprises from about 60% to about 70%, alternatively from about 61% to about 69%, alternatively from about 62% to about 68%, alternatively from about 63% to about 67%, of cations selected from calcium, strontium, magnesium and combinations thereof. In certain embodiments, the level of magnesium cations in the cationic salt function may be any combination of the ranges from about 1%, 5%, 10%, 15%, 20%, 25%, 30%, 35%, or 40% to about 20%, 25%, 30%, 35%, 40%, 45%, 50%, 55%, 60%, 61%, 62%, 63%, 64%, 65%, 66%. 67%, 68%, 69% or 70%, of the initial carboxyl groups reacted. In certain embodiments, the level of strontium cations in the cationic salt function may be any range combination from about 1%, 5%, 10%, 15%, 20%, 25%, 30%, 35%, or 40% to about 20%, 25%, 30%, 35%, 40%, 45%, 50%, 55%, 60%, 61%, 62%, 63%, 64%, 65%, 66%. 67%, 68%, 69% or 70%, of the initial carboxyl groups reacted. In certain embodiments, the level of calcium cations in the cationic salt function may be any combination of the ranges from about 1%, 5%, 10%, 15%, 20%, 25%, 30%, 35%, or 40% to about 20%, 25%, 30%, 35%, 40%, 45%, 50%, 55%, 60%, 61%, 62%, 63%, 64%, 65%, 66%. 67%, 68%, 69% or 70%, of the initial carboxyl groups reacted.

In certain embodiments, the cationic salt function may comprise from 0% to about 10%, alternatively from 0% to about 5%, alternatively from about 1% to about 4%; from about 1% to about 3%, or from about 0.5% to about 2% sodium cations.

In certain embodiments, the cationic salt function contains from about 25% to about 40% free acid component. In other embodiments, the free acid component may be any combination of the ranges from about 25%, 30%, 31%, 32%, 33%, 34%, 35%, 36%, 37%, 38%, or 39%, to about 30%, 31%, 32%, 33%, 34%, 35%, 36%, 37%, 38%, 39%, or 40%.

Such AVE/MA salts and methods of forming same are contemplated and described for example, in U.S. patent application Ser. Nos. 12/939,399 and 13/043,649 and U.S. Pat. Nos. 3,003,988, 4,569,955, 5,073,604, 5,872,161, 5,830,933, 6,025,411, 6,110,989, 6,239,191, 5,525,652, 5,753,723, and/or 5,304,616.

Suitable polymers used to make the AVE/MA salts include the grades AN169, AN179, and/or AN169BF from ISP Corp. Suitable AVE/MA salts include Ca(70)/Na(10) MVE/MA, Ca(70)/Na(5) MVE/MA, Ca(68) MVE/MA, Ca(65) MVE/MA, Ca(63) MVE/MA, Ca(63)/Na(5) MVE/MA, Ca(60)/Na (10) MVE/MA, Ca(47.5)/Zn(17.5) MVE/MA, and Ca(40)/Zn(20) MVE/MA, all made from AN169 and/or AN169 BF.

The alkyl vinyl ether maleic anhydride copolymers are obtained by co-polymerizing an alkyl vinyl ether monomer, such as methyl vinyl ether, ethyl vinyl ether, divinyl ether, propyl vinyl ether and isobutyl vinyl ether, with maleic anhydride to yield the corresponding alkyl vinyl ether-maleic anhydride copolymer which is readily hydrolyzable to the acid copolymer. Suitable copolymers may be prepared by well-known methods of the prior art, for example U.S. Pat. No. 2,782,182, and U.S. Pat. No. 2,047,398. Both anhydride and acid forms are also available from commercial suppliers.

For example, the ISP Corporation, Wayne, N.J. provides both the polymeric free acid form and the corresponding anhydride form under its "GANTREZ" trademark as the "GANTREZ S Series" and "GANTREZ AN Series", respectively. When the anhydride copolymer dissolves in water, the anhydride linkage is cleaved so that the highly polar, polymeric free acid is formed. Accordingly, the anhydride form, which is relatively less expensive than the acid form, may be used as a convenient and cheaper precursor for the acid. Elevated temperatures may be advantageously employed to enhance the rate of anhydride-to-acid hydrolysis.

The salt form of AVE/MA may be prepared by the interaction of the AVE/M anhydride or acid copolymer with at least one cationic salt function, such as magnesium, strontium, or calcium, and optionally sodium, compounds having a functional group typical of reactants of a carboxylic acid, such as, for example, the hydroxide, oxide, acetate, halide, lactate, etc. in an aqueous medium. In one embodiment, the magnesium oxide, strontium hydroxide, strontium carbonate, and/or calcium hydroxide are utilized.

In further embodiments, the denture adhesive composition comprises an additional adhesive component. In one embodiment, the additional adhesive component is present at the same levels and is selected from those listed for the adhesive component. In one embodiment, the additional adhesive component comprises a cellulose derivative. In a further embodiment, the cellulose derivative comprises sodium carboxymethylcellulose. In multiple embodiments, the additional adhesive component is present from about 5, 10, 15, 20% to about 30, 35, 40, 45, 50, 60%, or any combination thereof.

Cohesion Builder Component

In general, the denture adhesive compositions of the present disclosure comprise a denture adhesive component and a cohesion builder component. The cohesion builder component increases the cohesion of the denture adhesive component when hydrated.

It has been surprisingly found that certain cohesion builder components including Di-basic Sodium Phosphate [DSP], Tetra Sodium Pyro Phosphate [TSPP], and/or Sodium Tri Poly Phosphate [STPP] increase the cohesion of the denture adhesive component when hydrated, thus functioning as cohesion-builders. DSP is sometimes referred to as dibasic sodium phosphate, disodium hydrogen phosphate, disodium orthophosphate, sodium hydrogen phosphate, disodium monohydrogen phosphate, phosphoric acid disodium salt, sodium monohydrogen phosphate, disodium phosphate, disodium hydrogen orthophosphate, disodium phosphoric acid, sodium acid phosphate, soda phosphate di-basic sodium phosphate, di-basic sodium mono-phosphate, or di-sodium mono-phosphate.

The structures of these 3 components are given below.

DSP [CAS 7558-79-4]
TSPP [CAS 7722-88-5]
STPP [CAS 7758-29-4]

In certain embodiments, the cohesion builder component is selected from the group consisting of Di-basic Sodium Phosphate, Tetra Sodium Pyro Phosphate, and Sodium Tri Poly Phosphate, and mixtures thereof.

In certain embodiments, the cohesion builder component is selected from the group consisting of Di-basic Potassium Phosphate, Tetra Potassium Pyro Phosphate, and Potassium Tri Poly Phosphate, and mixtures thereof.

In certain embodiments, the cohesion builder component is selected from the group consisting of Phosphoric Acid, Pyro Phosphoric Acid, Tri Poly Phosphoric Acid, and mixtures thereof.

In certain embodiments, the cohesion builder component is selected from the group consisting of Di-basic Sodium Phosphate x-Hydrate, Tetra Sodium Pyro Phosphate x-Hydrate, and Sodium Tri Poly Phosphate x-Hydrate, and mixtures thereof, wherein x may vary from 0 to 20.

In certain embodiments, the cohesion builder component is selected from the group consisting of salts of mono-phosphates, salts of di-phosphates, salts of tri-phosphates, and mixtures thereof.

In certain embodiments, the cohesion builder component is selected from the group consisting of sodium salts of mono-phosphates, sodium salts of di-phosphates, sodium salts of tri-phosphates, and mixtures thereof.

In certain embodiments, the cohesion builder component is selected from the group consisting of potassium salts of mono-phosphates, potassium salts of di-phosphates, potassium salts of tri-phosphates, and mixtures thereof.

In certain embodiments, the cohesion builder component is a salt of mono-phosphate.

In certain embodiments, the cohesion builder component is a salt of mono-phosphate selected from the group consisting of sodium salt, potassium salt, and mixtures thereof.

In certain embodiments, the cohesion builder component is a salt of mono-phosphate selected from the group consisting of dibasic sodium mono-phosphate, dibasic potassium mono-phosphate, and mixtures thereof.

In certain embodiments, the cohesion builder component is dibasic sodium phosphate.

In certain embodiments, the cohesion builder component is selected from the group consisting of salts of mono-phosphates x-hydrate, salts of di-phosphates x-hydrate, salts of tri-phosphates x-hydrate, and mixtures thereof, wherein x may vary from 0 to 20.

In certain embodiments, the cohesion builder component is a sodium and/or potassium salt of phosphates wherein the phosphates are selected from the group consisting of phosphates with 1, 2, 3, 4, 5, 6, 7, 8, 9, 10, 15, 20, 25, 30, 35, or 40 phosphorous atoms, and mixtures thereof.

In certain embodiments, the cohesion builder component is a sodium and/or potassium salt of phosphates wherein the phosphates are selected from the group consisting of phosphates with 1, 2, 3, 4, or 5 phosphorous atoms, and mixtures thereof.

In certain embodiments, the cohesion builder component is a sodium and/or potassium salt of phosphates wherein the phosphates are selected from the group consisting of phosphates with 1, 2, 3, or 4 phosphorous atoms, and mixtures thereof.

In certain embodiments, the cohesion builder component is a sodium and/or potassium salt of phosphates wherein the phosphates may be phosphates with 1, 2, or 3 phosphorous atoms, and mixtures thereof.

In some embodiments, the cohesion builder component is a sodium and/or potassium salt of phosphates wherein the phosphates are selected from the group consisting of phosphates with 1, or 2 phosphorous atoms, and mixtures thereof.

In some embodiments, the cohesion builder component is a sodium and/or potassium salt of phosphates wherein the phosphates have 1 phosphorous atom.

In certain embodiments, cohesion builder components are used in an amount from about 0.01% to about 10.0%, about 0.05% to about 8.0%, about 0.10% to about 5.0%, about 0.25% to about 2.0%, about 0.50% to about 1.5%, or about 0.75% to about 1.25%. In certain embodiments, the cohesion builder components are present from about 0.01%, 0.05%, 0.10%, 0.25%, 0.50%, 0.75% to about 1.0%, 1.25%, 1.5%, 2.0% or 5.0%, 8.0%, 10% or any combination thereof.

In certain embodiments, the cohesion-builder component is physically mixed with the denture adhesive component.

In certain embodiments, the cohesion-builder component is chemically associated with the denture adhesive component. In certain embodiments, the cohesion-builder component (for example di-basic sodium phosphate) is chemically reacted with the denture adhesive component (for example AVE/MA salt).

Water Insoluble Component

In general, water-insoluble blends of mineral oil and petrolatum are used to make the composition into a suspension. This suspension of solid-particles in a liquid/gel vehicle/carrier is also referred to as a denture adhesive cream or paste. In certain embodiments, the present composition includes a safe and effective amount of a water insoluble component (wic). In one embodiment, this component is present by weight of the composition at an amount from about 2, 5, 10, 20, 25, 30, 35% to about 45, 50, 60, 70, 90%, or any combination thereof. In additional embodiments, the water insoluble component is present at an amount from about 20% to about 70%, from about 25% to about 60%, or from about 35% to about 60% by weight of the composition. In yet another embodiment, the water insoluble component is substantially non-swellable in water. In certain embodiments, the non-swellable water insoluble component swells less than about 10%, 5%, 2%, or 1% in water.

In one embodiment, the water insoluble component includes a liquid, gel, or mixtures thereof. In one embodiment, the water insoluble component is selected from the group consisting of: natural wax, synthetic wax, petrolatum, polyvinyl acetate, natural oils, synthetic oils, fats, silicone, silicone derivatives, dimethicone, silicone resins, hydrocarbons, hydrocarbon derivatives, essential oils, caprilic/capric triglycerides, polybutene, oleic acid, stearic acid, and combinations thereof. In a further embodiment, the water insoluble component comprises petrolatum, polyvinyl acetate, natural oils, synthetic oils, fats, silicone, silicone derivatives, dimethicone, silicone resins, hydrocarbons, hydrocarbon derivatives, polybutene, oleic acid, stearic acid, essential oils, caprilic/capric triglycerides, or combinations thereof.

Examples of natural oils include, but are not limited to, vegetable oils (ex. corn oil), soy bean oils, cottonseed oils, palm oils, coconut oils, mineral oils, animal oils (ex. fish oils), etc. Examples of synthetic oils include, but are not limited to, silicone oils, etc. In one embodiment, the water insoluble component comprises a natural oil. In an additional embodiment, the water insoluble component comprises 0% or less than 0.0001%, less than 0.001%, less than 0.01%, or less than 0.1%, by weight of the composition of petrolatum. In another embodiment, the water insoluble component further comprises petrolatum. In other embodiments, the water insoluble component may comprise mineral jelly, for example, mineral jellies numbers 4, 5, 10, 15, or 20 from Calumet Specialty Products.

In a further embodiment, the natural oil comprises mineral oil. In one embodiment, mineral oil is present in the composition at an amount from about 20% to about 50% and in another embodiment, from about 25% to about 45%. In certain embodiments, the mineral oil may be white, light, or technical. Light mineral oil may be, for example, Drakeol 5, 10, 13, or 15. White mineral oil may be, for example, Drakeol 19, 21, 34, 35, or 600.

In certain embodiments, the water insoluble component is a wax. Waxes are generally made up of various substances including hydrocarbons (normal or branched alkanes and alkenes), ketones, diketones, primary and secondary alcohols, aldehydes, sterol esters, alkanoic acids, terpenes (squalene) and monoesters (wax esters). Different types of waxes include animal and insect waxes (beeswax, Chinese wax, shellac wax, spermaceti, lanolin), vegetable waxes (bayberry wax, candelilla wax, carnauba wax, castor wax, esparto wax, Japan wax, jojoba oil, ouricury wax, rice bran wax), mineral waxes (cresin waxes, montan wax, ozocerite, peat waxes), petroleum waxes (paraffin wax or microcrystalline wax), and synthetic waxes (polyethylene waxes, Fischer-Tropsch waxes, chemically modified waxes, substituted amide waxes, polymerized $\alpha$-olefins).

In one embodiment the water insoluble component is a natural or synthetic wax. In a further embodiment, the natural wax is selected from the group consisting of: animal wax, vegetable wax, mineral wax, and combinations thereof. In another embodiment, the animal wax includes beeswax, lanolin, shellac wax, Chinese wax, and combinations thereof. In another embodiment, the vegetable waxes include carnauba, candelilla, bayberry, sugar cane, and combinations thereof; and mineral waxes include fossil or earth waxes (ozocerite, ceresin, montan), and petroleum waxes such as paraffin and microcrystalline wax, and combinations thereof. In one embodiment, the waxes herein are natural waxes selected from the group consisting of beeswax, candelilla, candela, carnauba, paraffin, and combinations thereof. In varying embodiments, wax can be present in an amount from about 1, 2, 5, 8% to about 10, 20, 30, 40%, or any combination thereof.

In another embodiment, the natural wax includes paraffin wax. A paraffin wax useful herein generally can have a melting point range of from about 65° C. to about 80° C. and, in another embodiment, from about 70° C. to about 75° C. In another embodiment, a microcrystalline wax useful herein can have a melting point of from about 65° C. to about 90° C., and, in another embodiment from about 80° C. to about 90° C. In one embodiment, a beeswax useful herein can have a melting point of from about 62° C. to about 65° C. and a flash point of 242° C. In another embodiment, a candelilla wax useful herein can have a melting point of from about 68° C. to about 72° C. In an additional embodiment, a carnauba wax useful herein can have a melting point of from about 83° C. to about 86° C. In one embodiment, a Fischer-Tropsch wax useful herein can have a melting point of about 95° C. to about 120° C. Synthetic grades of beeswax, candelilla, and carnauba waxes are also available with similar properties as the natural grades.

In one embodiment, the water insoluble component is petrolatum. According to Hawley's Condensed Chemical Dictionary 13$^{th}$ Edition, John Wiley & Sons, 1997, petrolatum is a "mixture of hydrocarbons derived by distillation of paraffin-base petroleum fractions"; and according to The United States Pharmacopia 2005, petrolatum is a "purified mixture of semisolid hydrocarbons obtained from petroleum". This is also referred to as "natural petrolatum". Petrolatum is stated to have a melting range between 38° C. and 60° C. according to The United States Pharmacopia 2005, and 38-54 C according to The Merck Index, 10$^{th}$ Edition, 1983. Petrolatums are available in a variety of grades with the "Cone Penetration Values" ranging from 180 to about 245 measured using ASTM D-937 according to the Sonneborn Inc product brochure.

In one embodiment, the water insoluble component has a melting point greater than about 60° C. In certain embodiments, the water insoluble thermoplastic component has a melting point from about 35° C., 40° C., 45° C., 50° C., 55° C., 60° C., 65° C., 70° C., 75° C., 80° C., 85° C., 90° C., 95° C., 100° C., to about 110° C., 120° C., 150° C., 175° C., 200° C. and/or any combination thereof to form a range, starting point, and/or end point. In another embodiment, the composition comprises 0% or less than 0.0001%, less than 0.001%, less than 0.01%, or less than 0.1%, by weight of the composition of a water insoluble thermoplastic component with a melting point above about 75° C.

In one embodiment, the water insoluble component is paraffin wax. The "Kirk-Othmer Encyclopedia of Chemical Technology", 5$^{th}$ Edition, vol. 26, page 216, hereby incorporated by reference, states that paraffin wax has the following typical properties: flash point, closed cup, 204° C.; viscosity at 98.9° C., 4.2-7.4; melting range, 46° C.-68° C.; refractive index at 98.9° C., 1.430 to 1.433; average molecular weight, 350 to 420; carbon atom per molecule, 20 to 26; and ductibility/crystallinity of solid wax, friable to crystalline, and in one embodiment, the water insoluble component has these particular properties.

In another embodiment, the water insoluble component is microcrystalline wax. In one embodiment, the microcrystalline wax is refined and/or substantially pure. In an additional embodiment, petrolatum does not contribute the microcrystalline wax. The "Encyclopedia of Polymer Science and Engineering", 2$^{nd}$ Edition, Vol. 17, page 788, hereby incorporated by reference, states that the molecular weight of microcrystalline wax ranges from 450 to 800. The "Kirk-Othmer Encyclopedia of Chemical Technology", 5$^{th}$ Edition, vol. 26, page 216, hereby incorporated by reference, states that microcrystalline wax has the following typical properties: flash point, closed cup, 260° C.; viscosity at 98.9° C., 10.2-25 mm$^2$/s; melting range, 60° C.-93° C.; refractive index at 98.9° C., 1.435 to 1.445; average molecular weight, 600 to 800; carbon atom per molecule, 30 to 75; and ductibility/crystallinity of solid wax, ductile-plastic to tough-brittle, and in one embodiment, the viscosity index improver has these particular properties.

Microcrystalline wax has been measured to have a total alkyl branching of about 12%, while petrolatum has about 43%, as measured using $^{13}$C-NMR.

In another embodiment, the microcrystalline wax has a melting point ranging from about 50° C. to about 100° C. In further embodiments, the microcrystalline wax has a melting point ranging from about 50° C., 55° C., 60° C., 65° C., 70° C. to about 70° C., 75° C., 80° C., 85° C., 90° C., 95° C., 100° C., or any combination thereof. In one particular embodiment, the microcrystalline wax has a melting point ranging from about 75° C. to about 85° C.

In another embodiment the microcrystalline wax is manufactured by Crompton, Sonneborn (Witco) and referred to and sold under the trademark Mutiwax®W-835. This wax has a melting point ranging from about 73.9° C. to about 79.4° C. (measured using ASTM D-127), has a penetration at 25° C. of from about 60 to about 80 (measured using ASTM D-1321), has a kinematic viscosity at 98.9° C. of from about 75 to about 90 saybolt universal seconds (measured using ASTM D-2161), has a flash point, COC (Cleveland open cup), of at least about 246° C. (measured using ASTM D-92), and has a congealing point from about 68° C. to about 77° C. (measured using ASTM D-938).

In another embodiment the microcrystalline wax is manufactured by Crompton, Sonneborn (Witco) and referred to and sold under the trademark Mutiwax®180W. This wax has a melting point ranging from about 79° C. to about 87° C. (measured using ASTM D-127), has a penetration at 25° C. of from about 15 to about 22 (measured using ASTM D-1321), has a kinematic viscosity at 98.9° C. of at least about 75 saybolt universal seconds (measured using ASTM D-2161), has a flash point, COC (Cleveland open cup), of at least about 277° C. (measured using ASTM D-92), and has a congealing point from about 75° C. to about 82° C. (measured using ASTM D-938).

In another embodiment the microcrystalline wax is manufactured by Crompton, Sonneborn (Witco) and referred to and sold under the trademark Mutiwax®W445. This wax has a melting point ranging from about 77° C. to about 82° C. (measured using ASTM D-127), has a penetration at 25° C. of from about 25 to about 35 (measured using ASTM D-1321), has a kinematic viscosity at 98.9° C. of from about 75 to about 90 saybolt universal seconds (measured using ASTM D-2161), has a flash point, COC (Cleveland open cup), of at least about 277° C. (measured using ASTM D-92), and has a congealing point from about 72° C. to about 77° C. (measured using ASTM D-938).

In one embodiment, the water insoluble component includes microcrystalline wax and is present at an amount from about 2% to about 30% and in another embodiment from about 5% to about 10%.

While microcrystalline wax and paraffin wax are both petroleum waxes, there are specific differences between them. Microcrystalline wax is a refined mixture of solid, saturated aliphatic hydrocarbons produced by de-oiling certain fractions from the petroleum refining process. In contrast to the more familiar paraffin wax which contains mostly unbranched alkanes, microcrystalline wax contains a higher percentage of isoparaffinic (branched) hydrocarbons and naphthenic hydrocarbons. It is characterized by the fineness of its crystals in contrast to the larger crystal of paraffin wax. It consists of high molecular weight saturated aliphatic hydrocarbons. It is generally darker, more viscous, denser, tackier and more elastic than paraffin waxes, and has a higher molecular weight and melting point. The elastic and adhesive characteristics of microcrystalline waxes are related to the non-straight chain components which they contain. Typical microcrystalline wax crystal structure is small and thin, making them more flexible than paraffin wax.

According to the "Encyclopedia of Polymer Science and Engineering" Volume 17 page 788, 1989 John Wiley & Sons): The molecular weights of paraffin waxes range from about 280 to 560 (C20 to C40); the molecular weights of microcrystalline wax range from 450 to 800 (C35 to C60). The amount of n-alkanes in paraffin wax usually exceeds 75% and can be as high as 100%; microcrystalline waxes are composed predominantly of iso-paraffinic and napthenic saturated hydrocarbons along with some n-alkanes.

According to Kirk-Othmer Encyclopedia of Chemical Technology, John Wiley & Sons, 2005: Paraffin Waxes have a number average molecular weight of 350-420 and carbons per molecule of 20-36; and Microcrystalline waxes have a number average molecular weight of 600-800 and carbons per molecule of 30-75. Paraffin wax is macrocrystalline, brittle, and is composed of 40-90% normal alkanes, with the remainder C18-C36 isoalkanes and cycloalkanes. A paraffin wax is a petroleum wax consisting principally of normal alkanes. Microcrystalline wax is a petroleum wax containing substantial proportions of branched and cyclic saturated hydrocarbons, in addition to normal alkanes. A classification system based on the refractive index of the wax and its congealing point as determined by ASTM D-938 has been developed. Paraffin waxes have a refractive index at 98.9 C of 1.430-1.433; and microcrystalline waxes have a refractive index at 98.9 C of 1.435-1.445. Paraffin waxes are friable to crystalline; microcrystalline waxes are ductile-plastic to tough-brittle. Paraffin wax has little affinity for oil; microcrystalline wax has great affinity for oil. Unlike paraffin wax, oil is held tightly in the crystal lattice of the microcrystalline wax, and does not migrate to the surface. Paraffin wax is stated to have a melting point of about 47-65° C., according to Hawley's Condensed Chemical Dictionary 13$^{th}$ Edition, John Wiley & Sons, 1997, and 46-68° C., according to Kirk-Othmer Encyclopedia of Chemical Technology, John Woley & Sons, 2005. Microcrystalline wax is stated to have a melting point of about 63-88° C., according to Hawley's Condensed Chemical Dictionary 13$^{th}$ Edition, John Wiley & Sons, and 60-93° C., according to according to Kirk-Othmer Encyclopedia of Chemical Technology, John Wiley & Sons, 2005.

Miscellaneous Additives

Plasticizer

The compositions of the present disclosure may also optionally include a safe and effective amount of one or more toxicologically-acceptable plasticizers. In varying embodiments the level of the plasticizer ranges from about 0.01% to about 10%. In another embodiment the plasticizer is water insoluble.

In certain embodiments, the denture adhesive composition, when extruded thermoplastically, does not cure and set as a result of the action of the plasticizer. In another embodiment the plasticizer does not solidify the water insoluble component or the denture adhesive composition. In another embodiment the water insoluble thermoplastic component does not cure and set.

In certain embodiments the denture adhesive composition may comprise 0% or less than 0.0001%, less than 0.001%, less than 0.01%, or less than 0.1% plasticizer by weight of the composition.

Plasticizers that may be used in the present invention include, but are not limited to one or more of the following: polyethylmethacrylate, triacetin, phthalic acid and its derivatives, glycerol triacetate, citric acid and its derivatives, phosphoric acid and its derivatives, glycol and its derivatives, paraffin wax, a pentaerythritol ester of a fatty acid, stearic acid and its derivatives, glycerol monostearate, polyethylene glycol, butyl phthalyl butyl glycolate, dimethyl phthalate, dibutyl phthalate, triacetin, triethyl citrate, acetyl triethyl citrate, acetyl tributyl citrate, triphenyl phosphate, diethylene glycol, caprylic triglyceride, capric triglyceride, propylene glycol dicaprylate/caprate, polyethylene, or glycerin.

Therapeutic Actives

The denture adhesive compositions may also include one or more therapeutic actives. Therapeutic actives may be present at a level of from about 0.01 to about 10%. Therapeutic actives include, for example, antimicrobial agents such as iodine, triclosan, peroxides, sulfonamides, bisbiguanides, or phenolics; antibiotics such as tetracycline, neomycin, kanamycin, metronidazole, cetylpyridinium chloride, domiphen bromide, or clindamycin; anti-inflammatory agents such as aspirin, acetaminophen, naproxen and its salts, ibuprofen, ketorolac, flurbiprofen, indomethacin, eugenol, or hydrocortisone; dentinal desensitizing agents such as potassium nitrate, strontium chloride or sodium fluoride; fluorides such as sodium fluoride, stannous fluoride, MFP (monofluorophosphate); anesthetic agents such as lidocaine or benzocaine; whitening agents such as peroxide; anti-fungals such as those for the treatment of *candida albicans*; insulin; steroids; herbal and other plant derived remedies; and baking soda. Other suitable therapeutic actives are discussed in the Physicians' Desk Reference 62$^{nd}$ Ed., 2008 and the Physicians' Desk Reference for non-prescription drugs, dietary supplements, and herbs, 29$^{th}$ Ed, (portions pertaining to non-prescription drugs, dietary supplements, and herbs are hereby incorporated by reference.)

In certain embodiments, the active is selected from the group consisting of: anti-calculus, fluoride ion source, stannous ion source, whitening, antimicrobial, anti-plaque, anti-stain, anti-deposition, anti-gingivitis, anti-tartar, anti-periodontitis, anti-sensitivity, anti-cavity, anti-inflammatory, nutrients, antioxidants, anti-viral, anti-fungal, analgesic, anesthetic, H-2 antagonist, and combinations thereof.

Flavor, Fragrance, and Sensate Actives

The compositions of the present invention may also include one or more components which provide flavor, fragrance, and/or sensate benefit (ex. warming or cooling agents). Suitable components include, for example, menthol, wintergreen oil, peppermint oil, spearmint oil, leaf alcohol, clove bud oil, anethole, methyl salicylate, eucalyptol, *cassia*, 1-8 menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal, their derivatives, and combinations thereof. In one embodiment, the active is an aromatic such as camphor, eucalyptus oil, and aldehyde derivatives such as benzaldehyde; or a combination thereof.

These agents may be present at a level of from about 0.01% to about 40%, in another embodiment from about 0.05 to about 5%, and in another embodiment from about 0.1 to about 2%, by weight of the composition.

Other Miscellaneous Additives

Other suitable ingredients include colorants and preservatives (such as methyl and propyl parabens, for example). In certain embodiments, the colorants and preservatives may be present at levels of from about 0.01 to about 20%, about 0.2 to about 10%, about 1% to about 5%, by weight of the composition, in certain embodiments from about 0.01%, 0.2, 1, 2, 5, to about 1, 5, 10, 20%, or any combination thereof. Additionally, the compositions may also include one or more solvents. These optional solvents may be miscible with the water insoluble component, and/or be capable of being dissipated in-situ. In certain embodiments, these solvents may be dissipated in-situ by evaporation, dissolution, dispersion, bio-absorption, or any other suitable means. In another embodiment, when the denture adhesive composition is an article, these solvents may be dissipated in-situ to leave behind a denture adhesive article. In one embodiment, solvents include silicones, hydrocarbons, iso-dodecane, iso-hexadecane, iso-eicosane, polyisobutene, or combinations thereof.

Denture Adhesive Composition

The denture adhesive composition can take many different forms. For example, the composition can be an emulsion, dispersion, slurry, gel, cream, paste, or combinations thereof. In one embodiment, the denture adhesive composition is in the form of a gel, cream, or paste. In another embodiment, the denture adhesive composition can be extruded out of a nozzle of a container like a tube, syringe, and/or pump, for example, directly onto a denture surface or a surface of the oral cavity.

The denture adhesive composition also has many properties, for example the composition may be bioerodible, non-aqueous, or a combination thereof.

In certain embodiments the composition comprises 0% or less than 0.0001%, less than 0.001%, less than 0.01%, or less than 0.1%, by weight of the composition of at least one of the following: zinc, phosphate molecules that contain 4 or more phosphorous atoms; polyphosphoric acids, their alkali salts and mixtures thereof; hexameta-polyphosphoric acid, their alkali salts and mixtures thereof; or hexameta-polyphosphoric acid that contain 4 or more phosphorous atoms, their alkali salts and mixtures thereof.

The denture adhesive composition and its components may contain any combination of elements and properties as disclosed herein.

Method of Manufacture

The compositions of the present invention may be prepared using processes well known in the art including those described in U.S. patent application Ser. Nos. 12/939,399 and 13/043,649 and U.S. Pat. Nos. 3,003,988, 4,569,955, 5,073,604, 5,872,161, 5,830,933, 6,025,411, 6,110,989, 6,239,191, 5,525,652, 5,753,723, and/or 5,304,616.

In general the denture adhesive component and cohesion-builder component are blended together to provide a powder form of denture adhesive. In general the denture adhesive component and cohesion-builder component are blended together with a water insoluble carrier such as mineral oil, petrolatum and/or microcrystalline wax with heating to provide a cream form of denture adhesive. In general the denture adhesive component and cohesion-builder component are blended together with a water insoluble carrier, such as microcrystalline wax with heating, extruded, and cut into shapes to provide a pre-formed article form of denture adhesive.

Examples of compositions of the present invention that may be prepared are shown below.

The denture adhesive compositions in CHART 1 (Samples A-K) can be made by blending together the following components. The amount of each component is shown by weight percent of the composition. Specifically, each of the denture adhesive samples in CHART 1 (A-K) can be prepared as follows: First connect a mixer with wall-scraper blades (Unimix from Haagen and Rinau) and hot water jacket to a water bath and a vacuum pump. Set the water bath of the hot water jacket to about 65° C. Add the mineral oil, petrolatum, and colorant to a mixer vessel. Turn on the agitator to about 30 RPM; mix until the composition temperature reaches about 65° C.; continue mixing for about an additional 10 minutes. Add the AVE/MA salt, carboxymethylcellulose, dibasic sodium phosphate (sieved through 200-mesh screen), and silica at about 30 to 50 RPM via a funnel to the mixer with the vent open. Close the vent and stop mixing. Scrape off powder clumps. Re-start mixing at about 70 RPM; continue mixing until the composition reaches about 65° C. Pull about 24 inches Hg vacuum and mix for about an additional 20 minutes under vacuum. Stop mixing, turn off the pump, slowly open the vent, release the vacuum, and raise the lid. Fill the sample into suitable containers, such as a foil tubes. The amount of each component is shown by weight percent of the composition.

CHART 1

| Components | Samples | | | | | | | | | | |
|---|---|---|---|---|---|---|---|---|---|---|---|
| | A | B | C | D | E | F | G | H | I | J | K |
| Mineral Oil, USP[1] | 24.53 | 24.53 | 24.53 | 24.53 | 24.53 | 24.53 | 24.53 | 24.53 | 24.53 | 24.53 | 24.53 |
| White Petrolatum, USP[2] | 21.26 | 21.22 | 21.17 | 21.02 | 20.77 | 20.52 | 20.27 | 20.02 | 19.77 | 19.27 | 16.27 |
| Carboxymethylcellulose Sodium, USP[3] | 20.00 | 20.00 | 20.00 | 20.00 | 20.00 | 20.00 | 20.00 | 20.00 | 20.00 | 20.00 | 20.00 |
| Silicon Dioxide, Colloidal, NF[4] | 1.14 | 1.14 | 1.14 | 1.14 | 1.14 | 1.14 | 1.14 | 1.14 | 1.14 | 1.14 | 1.14 |
| Any AVE/MA copolymer salt | 33.00 | 33.00 | 33.00 | 33.00 | 33.00 | 33.00 | 33.00 | 33.00 | 33.00 | 33.00 | 33.00 |
| Opatint Red Colorant OD1646[5] | 0.06 | 0.06 | 0.06 | 0.06 | 0.06 | 0.06 | 0.06 | 0.06 | 0.06 | 0.06 | 0.06 |

CHART 1-continued

| Components | Samples | | | | | | | | | | |
|---|---|---|---|---|---|---|---|---|---|---|---|
| | A | B | C | D | E | F | G | H | I | J | K |
| Dibasic Sodium Phosphate, USP[6] | 0.01 | 0.05 | 0.10 | 0.25 | 0.50 | 0.75 | 1.00 | 1.25 | 1.50 | 2.00 | 5.00 |
| | 100.00 | 100.00 | 100.00 | 100.00 | 100.00 | 100.00 | 100.00 | 100.00 | 100.00 | 100.00 | 100.00 |

[1]DRAKEOL 35 available from Penreco or KAYDOL from Sonneborn
[2]SNOW WHITE available from Penreco.
[3]CEKOL 30,000P available from CP Kelco.
[4]AEROSIL 200 available from Evonik Degussa.
[5]OPATINT RED OD 1646 available from Colorcon.
[6]Dibasic Sodium Phosphate, Anhydrous, USP [Product 7771-06, CAS 7558-79-4] available from Mallinckrodt/Macron/Avantor/J. T. Baker. [Contains 1 Phosphorous atom]

Samples A-Z of CHARTS 2-4 can be made as follows: First connect a mixer with wall-scraper blades (Unimix from Haagen and Rinau) and hot water jacket to a water bath and a vacuum pump. Set the water bath of the hot water jacket to about 95° C. Add the mineral oil, colorant, and microcrystalline wax to mixer vessel. Wait about 10 minutes, and after the Microcrystalline Wax has softened, turn on the agitator to about 30 RPM; mix until the composition temperature reaches about 90° C. Add the, carboxymethycellulose, at about 30 to 50 RPM via a funnel to the mixer with the vent open; continue mixing until the composition temperature returns to about 90° C. Close the vent and stop mixing. Scrape off powder clumps. Set the bath temperature to about 60° C. Re-start mixing at about 70 RPM. When the composition temperature reaches about 65° C., set the bath temperature to about 65° C. Stop mixing, add the AVE/MA salt, dibasic sodium phosphate (sieved through 200-mesh screen), and silica at about 30 to 50 RPM via funnel to the mixer with the vent open. Continue mixing at about 70 RPM. When the composition temperature returns to about 65° C., close the vent and pull about 24 inches Hg vacuum. Continue mixing under vacuum for about an additional 20 minutes. Stop mixing, turn off the pump, slowly open the vent, release the vacuum, and raise the lid. Fill the composition into suitable containers, such as a foil tubes.

CHART 2

| Components | Samples | | | | | | | | | | |
|---|---|---|---|---|---|---|---|---|---|---|---|
| | A | B | C | D | E | F | G | H | I | J | K |
| Light Mineral Oil[1] | 30.86 | 30.86 | 30.86 | 30.86 | 30.86 | 30.86 | 30.86 | 30.86 | 30.86 | 30.86 | 30.86 |
| Microcrystalline Wax W835[2] | 8.50 | 8.50 | 8.50 | 8.50 | 8.50 | 8.50 | 8.50 | 8.50 | 8.50 | 8.50 | 8.50 |
| Carboxymethylcellulose Sodium, USP[3] | 24.00 | 24.00 | 24.00 | 24.00 | 24.00 | 24.00 | 24.00 | 24.00 | 24.00 | 24.00 | 24.00 |
| Silicon Dioxide, Colloidal, NF[4] | 1.14 | 1.14 | 1.14 | 1.14 | 1.14 | 1.14 | 1.14 | 1.14 | 1.14 | 1.14 | 1.14 |
| Any AVE/MA copolymer salt | 35.49 | 35.45 | 35.40 | 35.25 | 35.00 | 34.75 | 34.50 | 34.25 | 34.00 | 33.50 | 30.50 |
| Dibasic Sodium Phosphate, USP[5] | 0.01 | 0.05 | 0.10 | 0.25 | 0.50 | 0.75 | 1.00 | 1.25 | 1.50 | 2.00 | 5.00 |
| | 100.00 | 100.00 | 100.00 | 100.00 | 100.00 | 100.00 | 100.00 | 100.00 | 100.00 | 100.00 | 100.00 |

[1]DRAKEOL 5 available from Penreco.
[2]MULTIWAX W-835 available from Sonneborn.
[3]CEKOL 30,000P available from CP Kelco.
[4]AEROSIL 200 available from Evonik Degussa.
[5]Dibasic Sodium Phosphate, Anhydrous, USP [Product 7771-06, CAS 7558-79-4] available from Mallinckrodt/Macron/Avantor/J. T. Baker. [Contains 1 Phosphorous atom]

CHART 3

| Components | Samples | | | | | | | | |
|---|---|---|---|---|---|---|---|---|---|
| | L | M | N | O | P | Q | R | S | T |
| Light Mineral Oil[1] | 32.11 | 32.11 | 32.11 | 32.11 | 32.11 | 32.11 | 32.11 | 32.11 | 32.11 |
| Microcrystalline Wax W835[2] | 7.25 | 7.25 | 7.25 | 7.25 | 7.25 | 7.25 | 7.25 | 7.25 | 7.25 |
| Carboxymethylcellulose Sodium, USP[3] | 24.00 | 24.00 | 24.00 | 24.00 | 24.00 | 24.00 | 24.00 | 24.00 | 24.00 |
| Silicon Dioxide, Colloidal, NF[4] | 1.14 | 1.14 | 1.14 | 1.14 | 1.14 | 1.14 | 1.14 | 1.14 | 1.14 |

CHART 3-continued

| Components | \multicolumn{9}{c}{Samples} | | | | | | | | |
|---|---|---|---|---|---|---|---|---|---|
| | L | M | N | O | P | Q | R | S | T |
| Any AVE/MA copolymer salt | 35.40 | 35.25 | 35.00 | 34.75 | 34.50 | 34.25 | 34.00 | 33.50 | 30.50 |
| Dibasic Sodium Phosphate, USP[5] | 0.10 | 0.25 | 0.50 | 0.75 | 1.00 | 1.25 | 1.50 | 2.00 | 5.00 |
| | 100.00 | 100.00 | 100.00 | 100.00 | 100.00 | 100.00 | 100.00 | 100.00 | 100.00 |

[1]DRAKEOL 5 available from Penreco.
[2]MULTIWAX W-835 available from Sonneborn.
[3]CEKOL 30,000P available from CP Kelco.
[4]AEROSIL 200 available from Evonik Degussa.
[5]Dibasic Sodium Phosphate, Anhydrous, USP [Product 7771-06, CAS 7558-79-4] available from Mallinckrodt/Macron/Avantor/J. T. Baker. [Contains 1 Phosphorous atom].

CHART 4

| Components | \multicolumn{6}{c}{Samples} | | | | | |
|---|---|---|---|---|---|---|
| | U | V | W | X | Y | Z |
| Light Mineral Oil[1] | 33.36 | 32.11 | 30.86 | 33.36 | 32.11 | 30.86 |
| Microcrystalline Wax W835[2] | 6.00 | 7.25 | 8.50 | 6.00 | 7.25 | 8.50 |
| Carboxymethylcellulose Sodium, USP[3] | 24.00 | 24.00 | 24.00 | 24.00 | 24.00 | 24.00 |
| Silicon Dioxide, Colloidal, NF[4] | 1.14 | 1.14 | 1.14 | 1.14 | 1.14 | 1.14 |
| Ca(65)/Na(0) MVE/MA Salt made from AN169BF | 34.50 | 34.50 | 34.50 | | | |
| Ca(70)/Na(5) MVE/MA Salt made from AN169BF | | | | 34.50 | 34.50 | 34.50 |
| Dibasic Sodium Phosphate, USP[5] | 1.00 | 1.00 | 1.00 | 1.00 | 1.00 | 1.00 |
| | 100.00 | 100.00 | 100.00 | 100.00 | 100.00 | 100.00 |

[1]DRAKEOL 5 available from Penreco.
[2]MULTIWAX W-835 available from Sonneborn.
[3]CEKOL 30,000P available from CP Kelco.
[4]AEROSIL 200 available from Evonik Degussa.
[5]Dibasic Sodium Phosphate, Anhydrous, USP [Product 7771-06, CAS 7558-79-4] available from Mallinckrodt/Macron/Avantor/J. T. Baker. [Contains 1 Phosphorous atom]

CHART 5

| Components | \multicolumn{11}{c}{Samples} | | | | | | | | | | |
|---|---|---|---|---|---|---|---|---|---|---|---|
| | A | B | C | D | E | F | G | H | I | J | K |
| Microcrystalline Wax W835[1] | 46.91 | 46.87 | 46.82 | 46.67 | 46.42 | 46.17 | 45.92 | 45.67 | 45.42 | 44.92 | 41.92 |
| Carboxymethylcellulose Sodium, USP[2] | 28.50 | 28.50 | 28.50 | 28.50 | 28.50 | 28.50 | 28.50 | 28.50 | 28.50 | 28.50 | 28.50 |
| Saccharin Sodium USP Powdered Fine | 0.08 | 0.08 | 0.08 | 0.08 | 0.08 | 0.08 | 0.08 | 0.08 | 0.08 | 0.08 | 0.08 |
| Any AVE/MA copolymer salt | 24.50 | 24.50 | 24.50 | 24.50 | 24.50 | 24.50 | 24.50 | 24.50 | 24.50 | 24.50 | 24.50 |
| Dibasic Sodium Phosphate, USP[3] | 0.01 | 0.05 | 0.10 | 0.25 | 0.50 | 0.75 | 1.00 | 1.25 | 1.50 | 2.00 | 5.00 |
| | 100.00 | 100.00 | 100.00 | 100.00 | 100.00 | 100.00 | 100.00 | 100.00 | 100.00 | 100.00 | 100.00 |

[1]MULTIWAX W-835 available from Sonneborn.
[2]CEKOL 30,000P available from CP Kelco.
[3]Dibasic Sodium Phosphate, Anhydrous, USP [Product 7771-06, CAS 7558-79-4] available from Mallinckrodt/Macron/Avantor/J. T. Baker. [Contains 1 Phosphorous atom].

Samples A-K of CHART 5 can be made as follows: The above compositions may be made by melting the Wax, adding the powders, mixing the ingredients, extruding the mixture into thin sheets, and cutting into suitable shapes to apply onto dentures.

Additional Example Denture Adhesive Compositions

Additional example compositions may be prepared by using the above formula percentages & making-procedures from Charts 1-5 with Tetra Sodium Pyrophosphate and/or Sodium Tri Poly Phosphate replacing all or part of the Dibasic Sodium Phosphate.

The above example compositions may also be blended with each other to provide hybrid examples. The levels of the various ingredients can also be increased or decreased by about 0%, 5%, 10%, 25%, 50%, 75%, or even 100%. Optionally, the grade of mineral oil may also be varied to include Drakeol 5, 10, 13, 15, 19, 21, 34, or 35 supplied by Calumet/Penreco or equivalent grades from other suppliers including Sonneborn/Witco. Optionally, the grade of microcrystalline wax can also be varied, including W445 or W180. The AVE/

MA copolymer salt can also be varied to include those comprising calcium, magnesium, sodium, zinc, strontium, iron, or mixtures thereof. Optionally, other colorants and/or flavors may also be added or omitted. Optionally, the order of addition of the ingredients and/or order of heating/cooling may also be varied.

EXAMPLES

The following examples further describe and demonstrate embodiments within the scope of the present disclosure. The examples are given solely for the purpose of illustration and are not to be construed as limitations of the present invention. Many variations of these are possible without departing from the spirit and scope of the invention.

Example 1

Each of the following denture adhesive Samples (A-E), shown in TABLE 1, were prepared to demonstrate the cohesion-building effect according to the present disclosure. Specifically, the following denture adhesive Samples (A-E), shown in TABLE 1, were prepared to demonstrate the cohesion-building effect of di-basic sodium phosphate, tetra sodium pyro phosphate, and sodium tri poly phosphate. The Samples were prepared using the following method—the "Ca(70)/Na(10) MVE/MA Salt made from AN169" was made using the following process:

Weigh 1890.84 grams of water into a 4-liter glass reaction vessel; hold back about 15% to wash down the sides of vessel. While mixing with a lab-stirrer, add 76.09 grams of MVE/MA Gantrez AN169, followed by 25.28 grams of Ca(OH)$_2$, followed by 7.80 grams of a 50% Solution of Na(OH). Heat the mixture with a heating mantle set to 88.5° C., while continuing to mix. After reacting at about 88.5° C. for about 2 hours, stop the mixing, pour the reacted solution into shallow stainless steel trays. Place trays in convection oven set at 70° C. and dry the solution for about 21 hours. Pull the trays out and remove the dried salt flakes. Mill the flakes in a Fritsch-mill using a 80 micron sieve. This powder is the "Ca(70)/Na(10) MVE/MA Salt made from AN169." In order to make Samples B, C, D, and E of TABLE 1, the phosphate was first sieved through a 200-mesh screen. The phosphate was then added to the "Ca(70)/Na(10) MVE/MA Salt made from AN169" in a 125 ml glass jar. This was then blended by manually shaking & turning the jar for a minimum of two minutes. The amount of each component is shown by weight in grams.

TABLE 1

| Components | Samples | | | | |
|---|---|---|---|---|---|
| | A | B | C | D | E |
| Ca(70)/Na(10) MVE/MA Salt made from AN169 | 16.50 | 16.50 | 16.50 | 16.50 | 16.50 |
| Dibasic Sodium Phosphate, USP[1] | | 0.50 | | | |
| Tetra Sodium Pyro Phosphate[2] | | | 0.50 | | |
| Sodium Tri Poly Phosphate, FCC[3] | | | | 0.50 | |
| Sodium Poly Phosphate, FCC (Glass H)[4] | | | | | 0.50 |

[1] Dibasic Sodium Phosphate, Anhydrous, USP [Product 7771-06, CAS 7558-79-4] available from Mallinckrodt/Macron/Avantor/J. T. Baker [Contains 1 Phosphorous atom].
[2] Sodium Pyro Phosphate Tetra, Anhydrous, FCC [Product TSPP, CAS 7722-88-5] available from Prayon Inc.[Contains 2 Phosphorous atoms]
[3] Sodium Tri Poly Phosphate, FCC [Product S1508, CAS 7758-29-4] available from Spectrum [Contains 3 Phosphorous atoms]
[4] Glass H Sodium Hexa Meta Phosphate Fines Food Grade [CAS 68915-31-1] [average chain length of 18 to 30 repeat-units] available from ICL Performance Products.[Contains 18 to 30 Phosphorous atoms]

Samples A-E of TABLE 1 were then evaluated for cohesion using the "Cohesion-Test" procedure described below. The results from this test-procedure are summarized below.

Cohesion Test Procedure

The Cohesion-Test Procedure is as follows:
1. A series of 7×4 dram vials is needed to make the dilution series listed below.
2. Weigh the powder to be cohesion-tested in the 4 dram glass vials, amounts listed below
3. Pre-weigh the distilled water into a 3 mL syringe, amounts listed below

| Ratio of Powder to Distilled Water | Powder (g) | Distilled Water (g) |
|---|---|---|
| 1 to 1 | 1.500 | 1.500 |
| 1 to 2 | 1.000 | 2.000 |
| 1 to 3 | 0.750 | 2.250 |
| 1 to 4 | 0.600 | 2.400 |
| 1 to 6 | 0.429 | 2.571 |
| 1 to 8 | 0.333 | 2.667 |
| 1 to 10 | 0.273 | 2.727 |

4. Place the vial on a counter-top vortex stirrer [VWR Analog Vortex Mixer]. Set the vortex stirrer to setting #10
5. Turn on the vortex stirrer and position the vial so that the powder swirls around inside the vial in a vortex form.
6. Add the pre-weighed distilled water into the 4 dram vial while vortex mixing. The addition shouldn't take more than approximately 0.5 second.
7. Mix the solution for 30 seconds or until the meniscus stops dropping, whichever comes first.
8. Tightly secure/snap the cap of the vial onto the vial.
9. Allow the mixtures to equilibrate for 30 minutes.
10. Turn the vial upside down and allow to sit for 18-24 hrs at 20-24° C.
11. Evaluate cohesiveness of the sample by the amount of the sample that flows down the sides of the glass vial by taking a picture of the vial. Generally, less cohesive samples flow down more, and vice-versa—so this is an indicator of the cohesion of the sample.

TABLE 2

| Samples | Dilution at which the gel has flowed down completely to the bottom of the vial | Extent of flow at a dilution of 1:4 | Improvement cohesion compared to Sample-A |
|---|---|---|---|
| A | 1:3 | Completely on bottom | n/a |
| B | 1:10 | Minimal flow from top | Yes |
| C | 1:6 | Minimal flow from top | Yes |
| D | 1:6 | Minimal flow from top | Yes |
| E | 1:3 | Completely on bottom | No |

Figure 1:
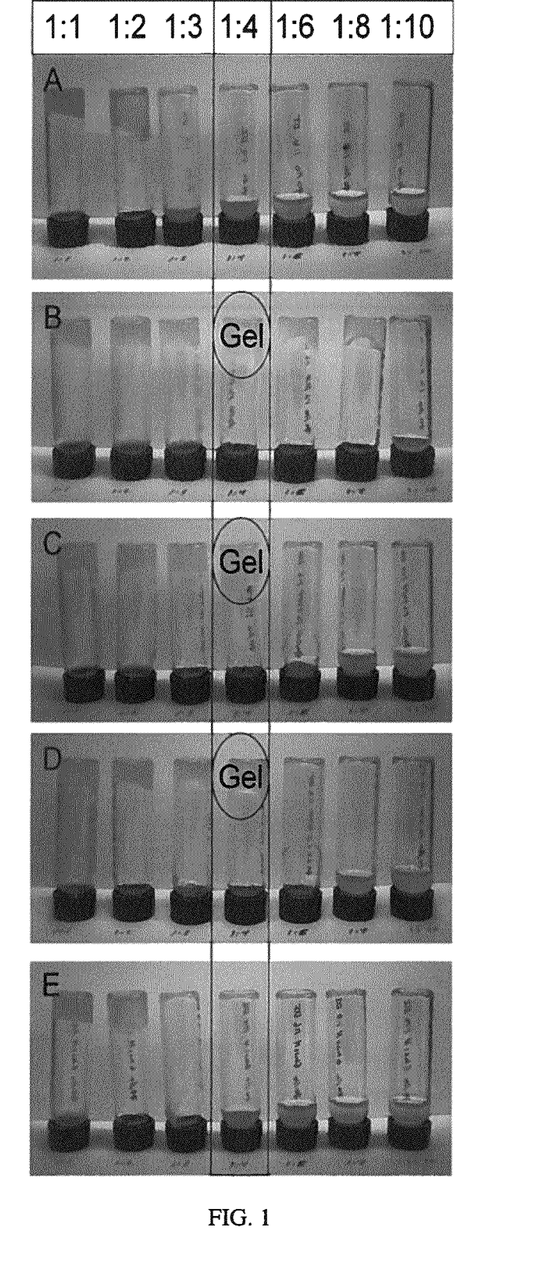
FIG. 1 is a photographic image of denture adhesive compositions in accordance with an embodiment of the present disclosure.

TABLE 2 and FIG. 1 show the results of the Cohesion-Test procedure for Samples A-E of TABLE 1. For each of the Samples A-E of TABLE 1, a total of 7 samples were prepared (as shown in FIG. 1 and further described below) at the following dilution levels (with distilled water—as described in the Cohesion Test Procedure): 1:1, 1:2, 1:3, 1:4, 1:6, 1:8, and 1:10. The cohesiveness of the samples was evaluated by the extent of flow at a fixed dilution. A dilution of 1:4 was chosen since it highlighted the differences between samples well. At this 1:4 dilution, less cohesive samples turned into a runny liquid and flowed down more while more cohesive samples exhibited minimal flow from the top (and remained as a cohesive gel instead). The cohesiveness of the samples were also evaluated by the lowest dilution at which the cohesive gel turned into a runny liquid and flowed down completely to the bottom of the vial—less cohesive samples did so at lower dilutions while more cohesive samples did so at higher dilutions. The cohesion-test results from TABLE 2 show that (Samples B, C & D) are more cohesive than (Sample A), when hydrated—because Samples B, C, D remained as cohesive gels at a dilution of 1:4 with minimal flow from the top, while sample A turned into a runny liquid that flowed down completely to the bottom of the vial at the same 1:4 dilution, and Samples B, C, D turned into a runny liquid that flowed down completely to the bottom of the vial only at a high dilutions of 1:10, 1:6, and 1:6 respectively while Sample A did so at a low dilution of 1:3. This demonstrates that di-basic sodium phosphate (Sample B), tetra sodium pyro phosphate (Sample C), and sodium tri poly phosphate (Sample D) increase the cohesion of the denture adhesive component (Ca(70)/Na(10) MVE/MA Salt), when hydrated. This further demonstrates that di-basic sodium phosphate, tetra sodium pyro phosphate, and sodium tri poly phosphate function as cohesion-builders.

The above results also show that Sample E is not more cohesive than Sample A, when hydrated—because Sample E turned into a runny liquid that flowed completely to the bottom of the vial at a fixed dilution of 1:4—same as Sample A; and, Sample E turned into a runny liquid at a low dilution of 1:3—similar to Sample A. This demonstrates that Sodium Poly Phosphate with an average chain length of 18 to 30 repeat-units (Sample E) does not increase the cohesion of the denture adhesive component (Ca(70)/Na(10) MVE/MA Salt), when hydrated. This further demonstrates that Sodium Poly Phosphate with an average chain length of 18 to 30 repeat-units does not function as a cohesion-builder.

Example 2

Each of the following denture adhesive samples (A-E), shown in TABLE 3, were prepared to demonstrate the cohesion-building effect according to the present disclosure. The samples were prepared using the following method—specifically, the following denture adhesive Samples (A-E), shown in TABLE 3, were prepared to demonstrate the cohesion-building effect di-basic sodium phosphate, and, lack of cohesion-building effect of Sodium Hexametaphosphates. The "Ca(70)/Na(10) MVE/MA Salt made from AN169" was made by reacting MVE/MA polymer (Product #AN169 from ISP) with Ca(OH)$_2$ & NaOH in the presence of water to yield a Ca(70)/Na(10) MVE/MA Salt solution. This solution was then dried on a drum-drier, Fitz-milled and finally Air-jet-milled This powder is the "Ca(70)/Na(10) MVE/MA Salt made from AN169" used in the samples A-D of TABLE 3. In order to make Samples B, C, D, and E of TABLE 3, the phosphate was first sieved through a 200-mesh screen. The phosphate was then added to the "Ca(70)/Na(10) MVE/MA Salt made from AN169" in a glass jar. This was then blended by manually shaking & turning the jar. The amount of each component is shown by weight in grams.

TABLE 3

| | Samples | | | | |
|---|---|---|---|---|---|
| Components | A | B | C | D | E |
| Ca(70)/Na(10) MVE/MA Salt made from AN169 | 33 | 33 | 33 | 33 | 33 |
| Dibasic Sodium Phosphate, USP[1] | | 1 | | | |
| Sodium Hexametaphosphate[2] [Contains 6 Phosphorous atoms per supplier] | | | 1 | | |
| Sodium Hexametaphosphate[3] [Contains 13 Phosphorous on average per supplier] | | | | 1 | |
| Sodium Hexametaphosphate[4] [Contains 17 to 22 Phosphorous atoms per supplier] | | | | | 1 |

[1]Dibasic Sodium Phosphate, Anhydrous, USP [Product 7771-06, CAS 7558-79-4] available from Mallinckrodt/Macron/Avantor/J. T. Baker [Contains 1 Phosphorous atom].
[2]Product#S2603 from Spectrum Chemicals, CAS 10124-56-8, $H_6O_{18}P_6Na_6$[Contains 6 Phosphorous atoms]
[3]Product#218 HexaPhos from ICL Performance Products, CAS 68915-31-1, $Na_{(n+2)}P_nO_{(3n+1)}$ with average n = 13 [Contains 13 Phosphorous atoms on average]
[4]Product# 440-FG PrayPhos from Prayon Inc, $(NaPO_3)_n$ with 16 < n < 22 [Contains 17 to 22 Phosphorous atoms]

Samples A-E of TABLE 3 were then evaluated for cohesion using the "Cohesion-Test" procedure, as described above in EXAMPLE 1. Sodium Hexametaphosphate samples were evaluated from 3 different suppliers—see TABLE 3 for details. The results from this test-procedure are shown below in TABLE 4.

TABLE 4

| Samples | Dilution at which the gel has flowed down completely to the bottom of the vial | Extent of flow at a dilution of 1:4 | Improvement in cohesion compared to Sample-A |
|---|---|---|---|
| A | 1:2 | Completely on bottom | n/a |
| B | 1:8 | Minimal flow from top | Yes |
| C | 1:3 | Completely on bottom | No |
| D | 1:3 | Completely on bottom | No |
| E | 1:3 | Completely on bottom | No |

Figure 2:
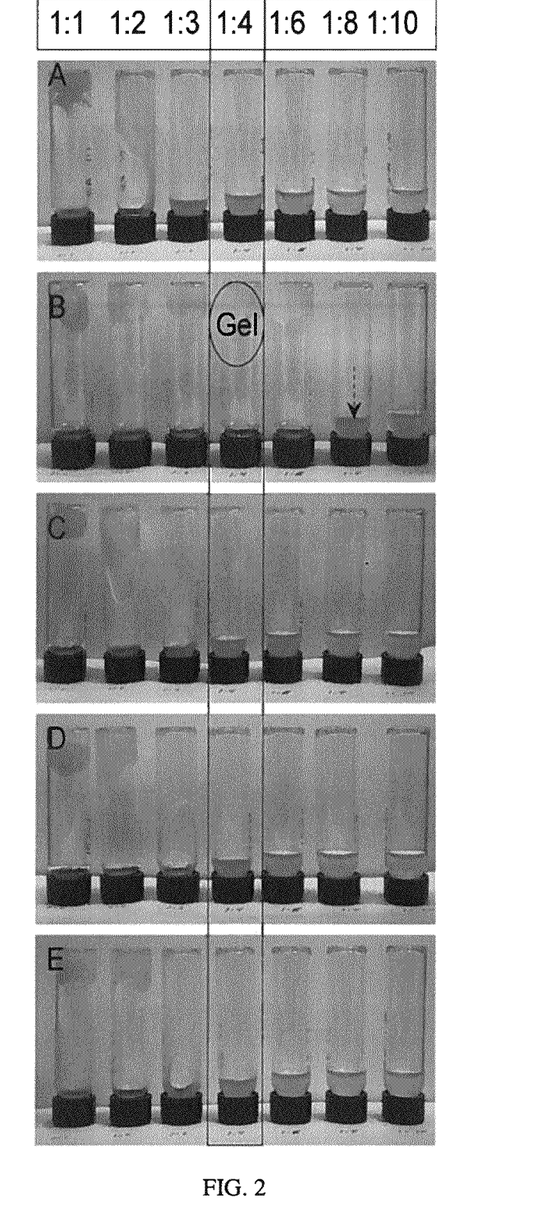
FIG. 2 is a photographic image of denture adhesive compositions in accordance with an embodiment of the present disclosure.

TABLE 4 and FIG. 2 show the results of the Cohesion-Test procedure for Samples A-E of TABLE 3. For each of the Samples A-E of TABLE 3, a total of 7 samples were prepared (as shown in FIG. 2 and further described below) at the following dilution levels (with distilled water—as described in the Cohesion Test Procedure): 1:1, 1:2, 1:3, 1:4, 1:6, 1:8, and 1:10. The cohesiveness of the samples was evaluated by the extent of flow at a fixed dilution. A dilution of 1:4 was chosen since it highlighted the differences between samples well. At this 1:4 dilution, less cohesive samples turned into a runny liquid and flowed down more while more cohesive samples exhibited minimal flow from the top (and remained as a cohesive gel instead). The cohesiveness of the samples were also evaluated by the lowest dilution at which the cohesive gel turned into a runny liquid and flowed down completely to the bottom of the vial—less cohesive samples did so at lower dilutions while more cohesive samples did so at higher dilutions. The cohesion-test results from TABLE 4 show that (Sample B) is more cohesive than (Sample A), when hydrated—because Sample B remained as a cohesive gel at a dilution of 1:4 with minimal flow from the top while sample A turned into a runny liquid that flowed down completely to the bottom of the vial at the same 1:4 dilution, and, Sample B turned into a runny liquid that flowed down completely to the bottom of the vial only at a high dilution of 1:8 while Sample A did so at a low dilution of 1:2. This demonstrates that di-basic sodium phosphate (Sample B) increases the cohesion of the denture adhesive component (Ca(70)/Na (10) MVE/MA Salt), when hydrated, further demonstrating that di-basic sodium phosphate functions as a cohesion-builder.

The above results also show that Samples C, D & E are not more cohesive than Sample A, when hydrated—because Samples C, D, and E turned into runny liquids that flowed completely to the bottom of the vial at a fixed dilution of 1:4—same as Sample A; and, Samples C, D, and E turned into a runny liquid at a low dilution—similar to Sample A. This demonstrates that Sodium Hexametaphosphates with 6 (Sample C), 13 (Sample D), or 17-21 (Sample E) phosphorous atoms do not increase the cohesion of the denture adhesive component (Ca(70)/Na(10) MVE/MA Salt), when hydrated. This further demonstrates that polyphosphates [also known as polyphosphoric alkali salts] such as Sodium Hexametaphosphates with 6, 13, or 17-21 phosphorous atoms do not function as a cohesion-builder.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A denture adhesive composition, comprising:
   a) a denture adhesive component in an amount from about 20.0% to about 70.0% by weight of the denture adhesive composition; wherein the denture adhesive component comprises a mixture of a partial salt of a copolymer of methyl vinyl ether-maleic acid and sodium carboxy methyl cellulose; and
   b) a cohesion builder component in an amount from about 0.1% to about 1.0% by weight of the denture adhesive composition; wherein the cohesion builder component is at least one of di-basic sodium phosphate, tetra sodium pyro phosphate, or sodium tri poly phosphate.

2. The denture adhesive composition according to claim 1, wherein the denture adhesive component further comprises at least one of cellulose, cellulose derivatives, starch, starch derivatives, saccharide, saccharide derivatives, polyethylene oxides, polyethylene glycols, polyvinyl alcohols, carrageenan, alginates, karaya gum, xanthan gum, guar gum, gelatin, algin, tragacanth, chitosan, acrylamide polymers, carboxypolymethylene, polyamines, polyquaternary compounds, polyvinylpyrrolidone, polymeric acids, polymeric salts, or polyhydroxy compounds.

3. The denture adhesive composition according to claim 1, wherein the denture adhesive component comprises a partial salt of a copolymer of alkyl vinyl ether-maleic acid containing a cationic salt function that is at least one of calcium, zinc, magnesium, strontium, iron, potassium, zirconium, or sodium.

4. The denture adhesive composition according to claim 1, wherein the denture adhesive component comprises a partial salt of a copolymer of alkyl vinyl ether-maleic acid or anhydride containing a cationic salt function having from about 60% to about 72% calcium cations; from about 0% to about 10% sodium cations; and from about 20% to about 40% of a free acid component.

5. The denture adhesive composition according to claim 1, further comprising a water insoluble component that is at least one of water insoluble liquids or water insoluble thermoplastic components.

6. The denture adhesive composition according to claim 5, wherein the water insoluble component is at least one of microcrystalline wax, mineral oil, petrolatum, silicones, or hydrocarbons.

7. The denture adhesive composition according to claim 1, wherein the composition comprises less than 0.1% by weight of the composition of phosphate molecules that have more than three phosphorous atoms.

8. The denture adhesive composition according to claim 1, wherein the composition does not contain phosphate molecules that have more than three phosphorous atoms.

9. The denture adhesive composition according to claim 1, wherein the composition comprises less than 0.1% zinc by weight of the composition.

10. The denture adhesive composition according to claim 1, wherein the composition does not contain zinc.

11. A denture adhesive composition, comprising:
    a) a denture adhesive component in an amount from about 20.0% to about 70.0% by weight of the denture adhesive composition; wherein the denture adhesive component comprises a mixture of a partial salt of a copolymer of methyl vinyl ether-maleic acid and sodium carboxy methyl cellulose; wherein the partial salt of copolymer of methyl vinyl ether-maleic acid contains a cationic salt function having from about 60% to about 72% calcium cations; from about 0% to about 10% sodium cations; and from about 20% to about 40% of a free acid component;
    b) a cohesion builder component from about 0.1% to about 2.0% about 0.1% to about 1.0% of the denture adhesive composition, wherein the cohesion builder component comprises di-basic sodium phosphate; and
    c) a water insoluble component from about 20% to about 70% by weight of the denture adhesive composition.

12. The denture adhesive composition according to claim 11, wherein the composition comprises less than 0.1% by weight of the composition of phosphate molecules that have more than three phosphorous atoms.

* * * * *